(12) United States Patent
Kratz et al.

(10) Patent No.: US 7,462,167 B2
(45) Date of Patent: Dec. 9, 2008

(54) CATHETER SHEATH SLITTER AND METHOD OF USE

(75) Inventors: Doug Kratz, Chester Springs, PA (US); Andrew W. Armour, Media, PA (US); Christopher A. Heine, Schwenksville, PA (US); Seth Worley, Lancaster, PA (US)

(73) Assignee: Thomas Medical Products, Inc., Malvern, PA (US)

( * ) Notice: Subject to any disclaimer, the term of this patent is extended or adjusted under 35 U.S.C. 154(b) by 442 days.

(21) Appl. No.: 11/043,783

(22) Filed: Jan. 26, 2005

(65) Prior Publication Data

US 2006/0167417 A1 Jul. 27, 2006

(51) Int. Cl.
*A61M 5/178* (2006.01)

(52) U.S. Cl. ............... 604/164.05; 604/158; 604/160; 604/164.01; 30/90.4; 30/90.8

(58) Field of Classification Search ............ 604/158, 604/159, 160, 164.01, 164.05; 30/90.4, 90.8
See application file for complete search history.

(56) References Cited

U.S. PATENT DOCUMENTS

| | | | | |
|---|---|---|---|---|
| 3,043,004 | A | * | 7/1962 | Leland .................. 30/92.5 |
| 3,238,618 | A | * | 3/1966 | Cook, Jr. ................ 30/90.4 |
| 4,198,751 | A | * | 4/1980 | Egbert .................... 30/286 |
| 4,507,867 | A | * | 4/1985 | Haas, Jr. ................ 30/90.4 |
| 4,687,469 | A | | 8/1987 | Osypka |
| 4,997,424 | A | * | 3/1991 | Little ..................... 604/161 |
| 5,188,606 | A | * | 2/1993 | Maloney et al. ........ 604/161 |
| 5,322,513 | A | | 6/1994 | Walker |
| 5,330,460 | A | * | 7/1994 | Moss et al. .............. 30/90.4 |
| 5,687,727 | A | | 11/1997 | Kraus et al. |
| 5,713,867 | A | | 2/1998 | Morris |
| 5,951,518 | A | | 9/1999 | Licata et al. |
| 6,159,198 | A | | 12/2000 | Gardeski et al. |
| 6,280,433 | B1 | | 8/2001 | McIvor et al. |
| 6,379,346 | B1 | * | 4/2002 | McIvor et al. ........... 604/524 |
| 6,497,681 | B1 | * | 12/2002 | Brenner ................ 604/164.05 |
| 6,510,611 | B2 | * | 1/2003 | Edwards et al. .......... 30/90.6 |
| 7,029,460 | B2 | * | 4/2006 | Gardeski et al. ......... 604/160 |

\* cited by examiner

*Primary Examiner*—Nicholas D Lucchesi
*Assistant Examiner*—Quynh-Nhu H Vu
(74) *Attorney, Agent, or Firm*—Caesar, Rivise, Bernstein, Cohen & Pokotilow, Ltd.

(57) ABSTRACT

A device and method for slitting a first elongated flexible catheter/sheath used with an elongated flexible component. The device includes a handle, an elongated groove and a cutter member. The cutter member has a sharp distally located cutting edge and a top surface from which a finger projects distally. The cutting edge is located under the finger and is arranged to be located within the annular space between the component and the first catheter/sheath when the first catheter/sheath is within the groove. The cutting edge serves to slice the first catheter/sheath longitudinally when the first catheter/sheath is pulled in a proximal direction. The finger protects the component from injury.

19 Claims, 10 Drawing Sheets

CATHETER SHEATH SLITTER AND METHOD OF USE

BACKGROUND OF THE INVENTION

This invention relates generally to medical devices, and more particularly to devices and methods of use for removing a catheter, e.g., an introducer sheath, or other elongated tubular member which has been used to place a cardiac pacemaker (pacing) lead or other elongated intravascular instrument at a desired position within the body of a patient and without disturbing that pacing lead or instrument.

In current electrophysiology practice, the physician typically uses both hands to grasp and peel or split an introducer sheath to remove it from a cardiac pacing lead that has been positioned through the sheath to a desired location within the patient's body. A second person is sometimes used to hold the pacing lead in the desired position while the sheath is removed to ensure that the pacing lead is not displaced or moved. Alternatively, and more commonly, the physician holds the pacing lead with one hand, and withdraws the introducer sheath a short distance with the other hand. Then the physician grasps each half of the split peel-away hub and peels the sheath apart a short distance further. Once this is accomplished the physician again holds the pacing lead a little further up, and withdraws the introducer sheath a short distance further. This incremental series of motions is repeated several times until the introducer sheath is completely removed from the patient and the pacing lead, to minimize any displacement of the pacing lead.

A primary concern of the physician during this repetitive procedure centers around the numerous manipulations necessary to remove the introducer from the pacing lead, and the significant potential for moving the freshly placed tip of the pacing lead, since some pacing leads exhibit a tendency to move out of position if the lead is pulled or otherwise disturbed.

In U.S. Pat. No. 6,497,681 (Brenner), which is assigned to the same assignee as this invention there is disclosed a holding device for use with an elongated flexible member, e.g., a cardiac pacing lead, and a tubular introducer member, e.g., a peelable or tearable introducer sheath or catheter. The tubular introducer member is arranged to be extended into the body of a living being, with the elongated flexible member arranged to extend through the tubular introducer member into the being's body for location at a desired position. The tubular introducer member is arranged to be withdrawn proximally from the being's body after the elongated flexible member is in the desired position. The elongated flexible member has a proximal portion that deters the tubular introducer member from being withdrawn out of the being's body while the elongated flexible member is in place extending through the tubular introducer member. The holding device basically comprises a first portion, e.g., a "gripper" portion, and a second portion, e.g., a "splitter" portion. The first portion includes at least one contoured engagement surface or jaw to grasp a portion of the periphery of the elongated flexible member to hold the elongated flexible member at the desired position within the being's body. The second portion is arranged to cause the tubular introducer member to separate longitudinally. In particular, the second portion includes a sharp edge portion for engaging the tubular introducer member to split the tubular introducer member longitudinally, when the tubular introducer member is withdrawn, e.g., pulled proximally with respect to the holding device, as the holding device is held in place gripping the elongated flexible member. Once it is separated, e.g., split, longitudinally, the tubular introducer member can be removed from the elongated flexible member leaving the elongated flexible member at the desired position within the being's body.

Other U.S. patents relating to devices/methods for splitting catheters or sheaths are: U.S. Pat. No. 4,687,469 (Osypka), U.S. Pat. No. 4,997,424 (Little), U.S. Pat. No. 5,188,606 (Maloney et al.), U.S. Pat. No. 5,322,513 (Walker), U.S. Pat. No. 5,330,460 (Moss et al.), U.S. Pat. No. 5,687,727 (Kraus et al.), U.S. Pat. No. 5,713,867 (Morris), U.S. Pat. No. 5,951,518 (Licata et al.), U.S. Pat. No. 6,159,198 (Gardeski et al.), U.S. Pat. No. 6,280,433 (McIvor et al.), and U.S. Pat. No. 6,379,346 (McIvor, et al.).

While the aforementioned prior art devices may be suitable for their intended purposes they nevertheless leave something to be desired from one or more of the standpoints of simplicity of construction, ease of use and effectiveness.

SUMMARY OF THE INVENTION

A device and method of splitting a first elongated flexible catheter used with a flexible elongated component, e.g., a pacing lead. The first catheter has an interior surface. The component has an exterior surface and is arranged to be extended through the first catheter, whereupon an annular space between the inner surface of the first catheter and the outer surface of the component results. The splitter device basically comprises a handle, a receiving surface, e.g., an elongated groove, and a cutter member. The receiving surface has a longitudinal axis and is arranged to receive a proximal end portion of the outer periphery of the catheter thereon. The cutter member projects upward from the receiving surface and has a sharp distally located cutting edge and a top surface from which a finger projects in a distal direction beyond the distally located cutting edge. The finger is arranged to be located within the annular space between the component and the first catheter when the first catheter is disposed on the receiving surface. The distally located cutting edge is arranged to slit the first catheter when the device is moved distally with respect to the catheter.

In accordance with one preferred aspect of this invention the groove includes a distally located portion and a proximally located portion. The distally located portion of the groove is of semicircular cross-section and has a radius of curvature approximately equal to that of the outer surface of the first catheter. The proximally located portion of the groove is of semicircular cross-section and has a radius of curvature approximately equal to that of the outer surface of the component. The proximally located portion of the groove is arranged to receive a proximal portion of the component as the first catheter is slit to enable the thumb of a user of the slitting device to hold the component in place.

In accordance with another preferred aspect of this invention the groove includes a portion having a pair of contiguous walls that flare in the proximal direction and are arranged to separate the slit portions of the sheath.

In accordance with yet another aspect of this invention the slitting device is arranged to be used with a second, e.g., outer catheter. The second catheter is arranged to be extended into the body of the being, with the first, e.g., inner, catheter extending through the second, e.g., outer, catheter. The second catheter includes a hub. The slitting device additionally comprises a retaining member located adjacent the distal end portion of the receiving surface, e.g., groove. The retaining member, e.g., a C-shaped ring, is adapted to receive and hold the hub of the second catheter.

This invention also entails a method of slitting the first catheter.

DETAILED DESCRIPTION OF THE PREFERRED EMBODIMENT

Figure 1:
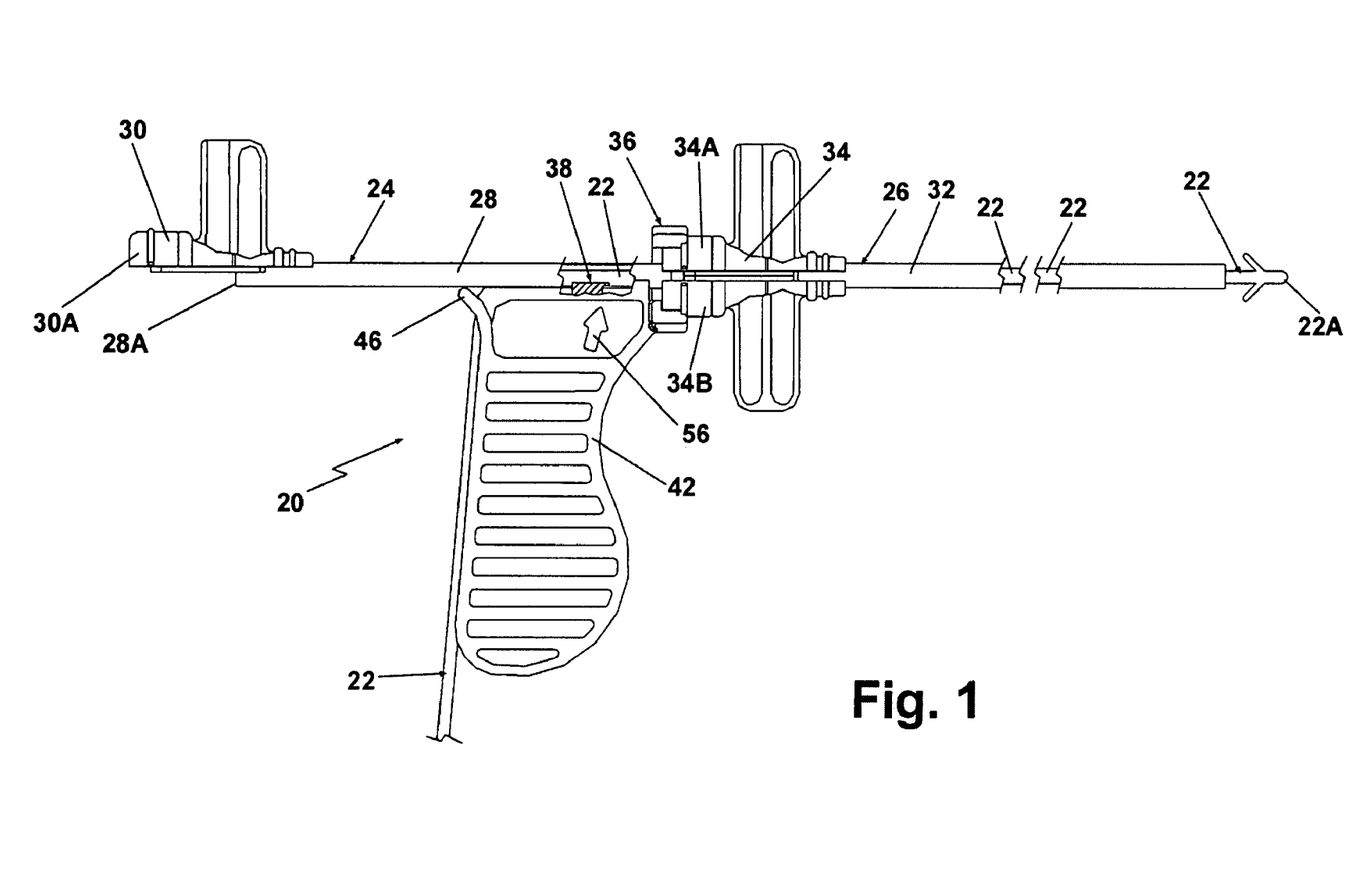
FIG. 1 is a side elevation view, partially broken away, showing one exemplary splitting or slicing device of the subject invention being used with a conventional cardiac pacing lead located extending through two elongated flexible catheters or sheaths, i.e., an inner catheter/sheath and an outer catheter/sheath.
Figure 10:
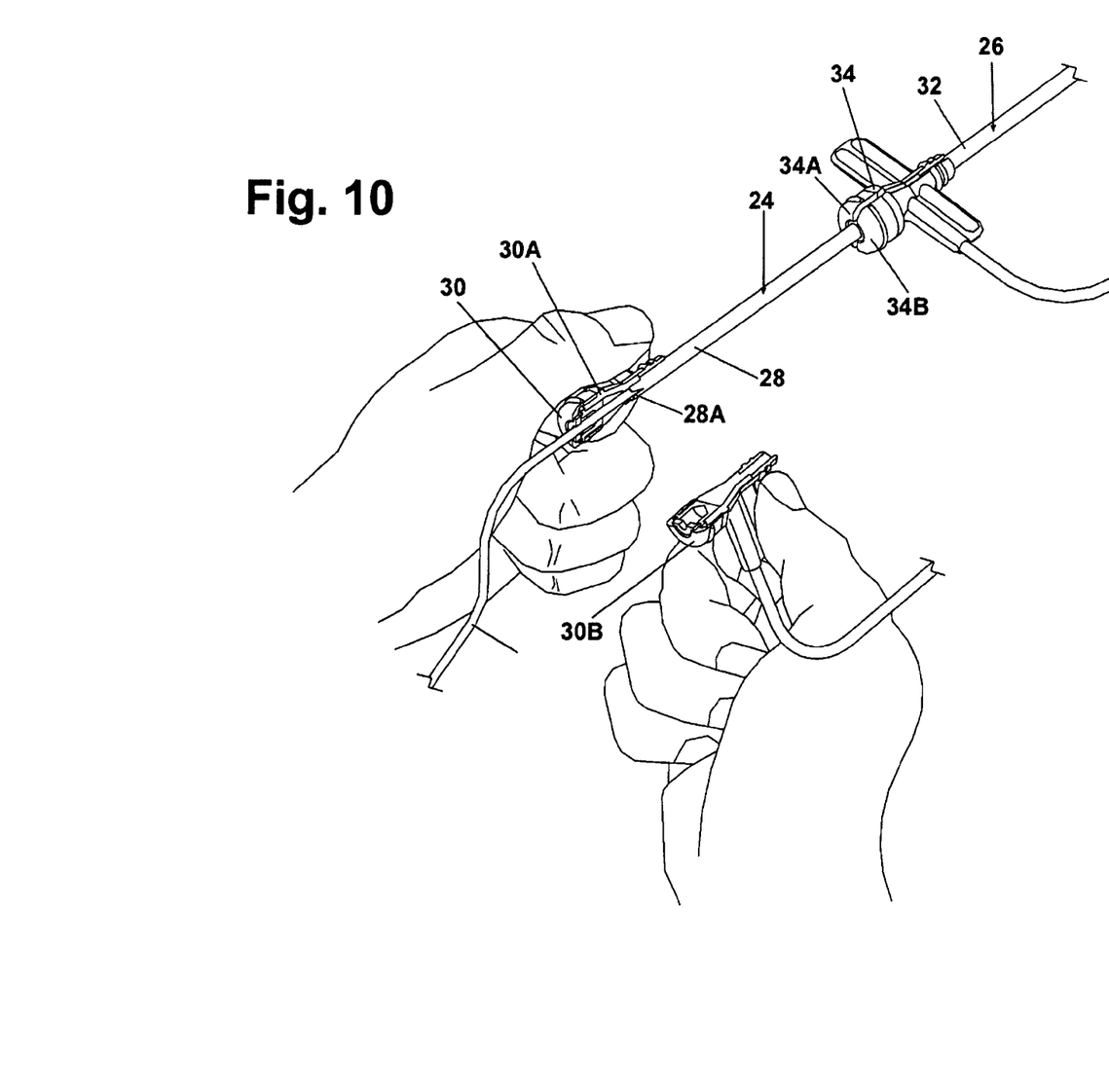
FIG. 10 is an illustration showing an initial step in the use of the device with the pacing lead and two catheter/sheaths like shown in FIG. 1 to effect the removal of the inner catheter/sheath.

Referring now to the various figures of the drawing wherein like reference characters refer to like parts, there is shown at 20 in FIG. 1 a splitting or slicing device constructed in accordance with one preferred exemplary embodiment of this invention for use with an elongated flexible member, e.g., a cardiac pacing lead 22 or other elongated flexible instrument or catheter, that is extended through at least one catheter/sheath or other tubular instrument. In the embodiment shown there are two generally tubular instruments, namely, an inner catheter/sheath 24 and an outer catheter/sheath 26. Such an arrangement particularly useful for treating patients with congestive heart failure via heart-resynchronization by means of biventricular pacing. As will be appreciated by those skilled in the art this technique is commonly accomplished by gaining access to the patient's vascular system via either the jugular, subclavian or axial vein, down through the superior vena cava to the right atrium and into the ostium to the coronary sinus by means of the outer catheter or introducer sheath 26. The outer catheter/sheath includes a somewhat flexible tubular body 32 and a hub 34 at its proximal end. Although not shown, the distal end of the outer catheter/sheath is preferably curved to facilitate steering. In order to traverse into a desired branched vessel off of the coronary sinus, an inner catheter or introducer sheath is sometimes used. The inner catheter/sheath 24 includes a somewhat flexible tubular body 28 and a hub 30 (only half of which 30A is shown in FIG. 1) at its proximal end. The other half of the hub 30 is designated by the reference number 30B and is shown in FIG. 10. Although not shown, the distal end of the inner catheter/sheath 24 is also preferably curved to facilitate steering.

The inner catheter/sheath 24 is extended through the outer catheter/sheath 26 so that the distal end of the inner catheter/sheath enters into the desired vessel branch. In order to effectively navigate the passage to the desired position the tubular body of the inner catheter/sheath is typically a reinforced (e.g., braided) member for enhanced torsional, rotational and steering capabilities. The hub 30 of the inner catheter/sheath can be a splitable member, e.g., can be composed of two sections 30A and 30B that can be readily split or separated from each other by the user breaking them apart. Alternatively, the hub may be an integral unit which includes a thin or reduced wall region (not shown) that is arranged to be cut longitudinally to split the hub. In another alternative, the hub may be single-sided (e.g., connected to only one side of the sheath) and not be splitable.

When the outer catheter/sheath 26 and the inner catheter/sheath 24 are in place, the distal end of the inner catheter/sheath extends beyond the distal end of the outer catheter/sheath and the proximal end of the inner catheter/sheath extends beyond the proximal end of the outer catheter/sheath. The pacing lead 22 extends through the inner catheter/sheath 24, with its distal end 22A extending beyond the distal end of the inner catheter/sheath 24 to the desired position. The pacing lead 22 includes a hub (not shown) at its proximal end which is located proximally of the hub 30 of the inner catheter/sheath 24 when the pacing lead 22 is in place.

Once the pacing lead is in place it is necessary to remove the inner catheter/sheath 24 and the outer catheter/sheath 26 without disturbing the pacing lead. Such action requires the splitting of those catheter/sheaths since neither can be slid off of the hub at the proximal end of the pacing lead. The removal action can be accomplished through the use of a catheter/sheath which is constructed to be inherently divisible, e.g., the body includes at least one longitudinally weakened or frangible line which can be broken by the application of a force to it. If, however, the body of the catheter/sheath is not inherently splitable, such as is the case with a braided reinforced catheter/sheath like catheter/sheath 24, then some device for cutting the braided body 28 of the catheter/sheath longitudinally is required. The device 20 of this invention is particularly suitable for accomplishing such action.

Before describing the details of the splitting/slicing device 20 and its methods of use, it should be pointed out that the splitting/slicing device 20 can be used for applications involving use of a pacing lead and a single catheter/sheath 24 or some other elongated tubular member through which the pacing lead 22 extends and which catheter/sheath or other tubular member must be removed after proper location of the pacing lead. In fact, the splitting/slicing device 20 of this invention can be used with elongated device/instruments other than pacing leads. Thus, the subject invention can be used for any application wherein an elongated instrument is extended through a catheter/sheath or tubular member into the body of a living being to accomplish some procedure, and wherein the catheter/sheath or tubular member must be removed by being split or cut after placement of the elongated instrument therethrough.

In the exemplary embodiment shown in FIG. 1, the cardiac pacing lead 22 is of conventional construction including a proximally located hub or structure (not shown) and the heretofore identified elongated flexible body 22 terminating in a distal end 22A. The inner catheter/sheath 24 is also of conventional construction and, as mentioned earlier, has a tubular, reinforced body 28 and a proximally located hub 30. The tubular body 28 comprises a flexible plastic tube which is reinforced internally by metal or some other strong material braiding (not shown). The outer catheter/sheath 26 is also of conventional construction and includes a tubular body 32 and a proximally located hub 34. The hub 34 may be constructed similarly to hub 30, namely, be splitable by means of a pair of sections 34A and 34B to facilitate its removal from the body of the patient after the inner catheter/sheath 24 has been removed.

As mentioned earlier the inner catheter/sheath 24 is arranged to be located so that its tubular body 28 extends through the tubular body 32 of the outer catheter/sheath 26. The elongated body of the pacing lead 22 is arranged to be extended through the inner catheter/sheath 24 so that its distal end 22A extends beyond the distal end of the tubular body of the inner catheter/sheath (and hence beyond the distal end of the tubular body of the outer catheter/sheath 32). Since the pacing lead 22, the inner catheter/sheath 24 and the outer catheter/sheath 26 are all conventional devices, further details of their structure and operation will not be given herein in the interest of brevity.

Figure 11:
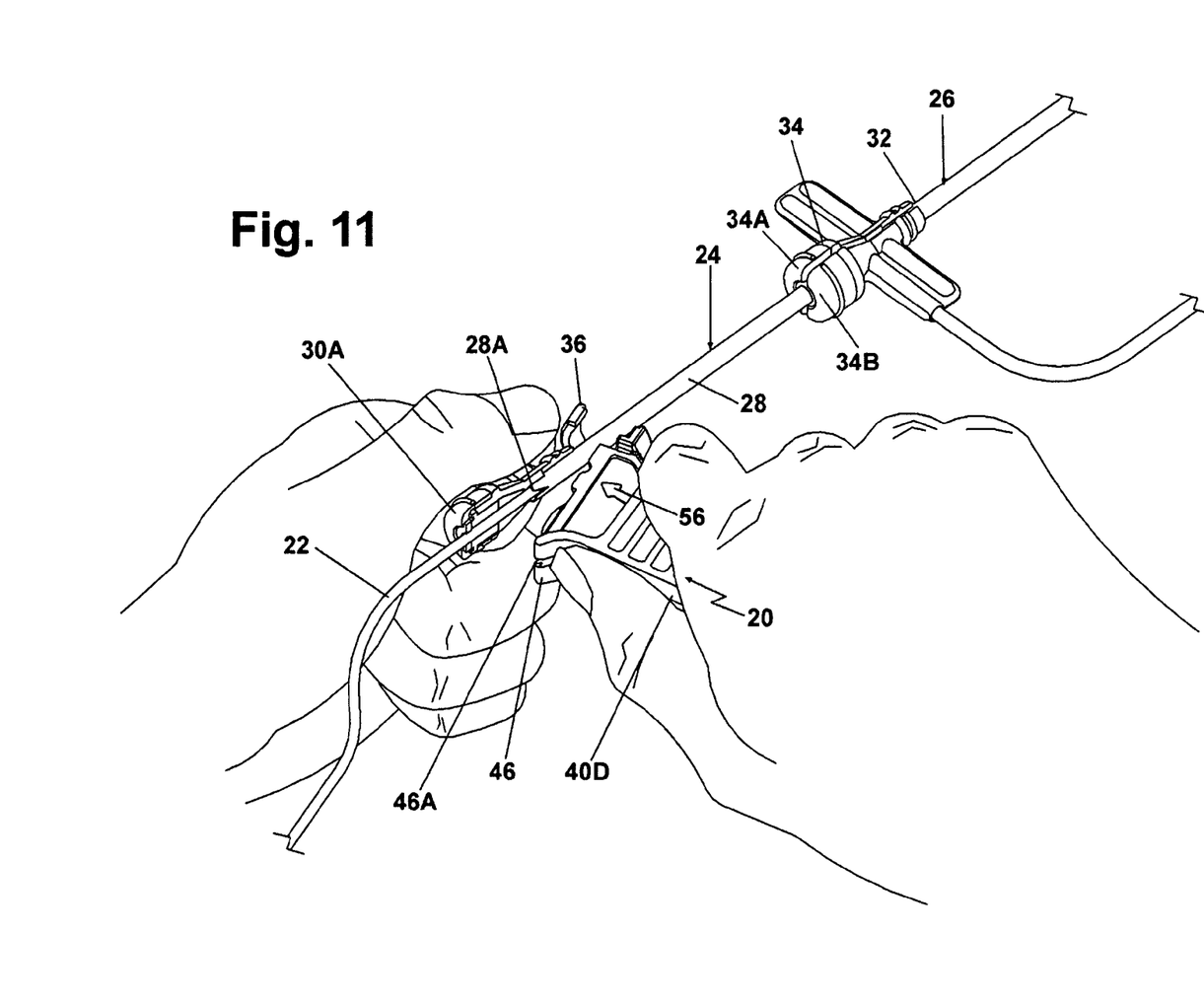
FIG. 11 is an illustration, like that of FIG. 10, but showing a subsequent step in the removal of the inner catheter/sheath.
Figure 12:
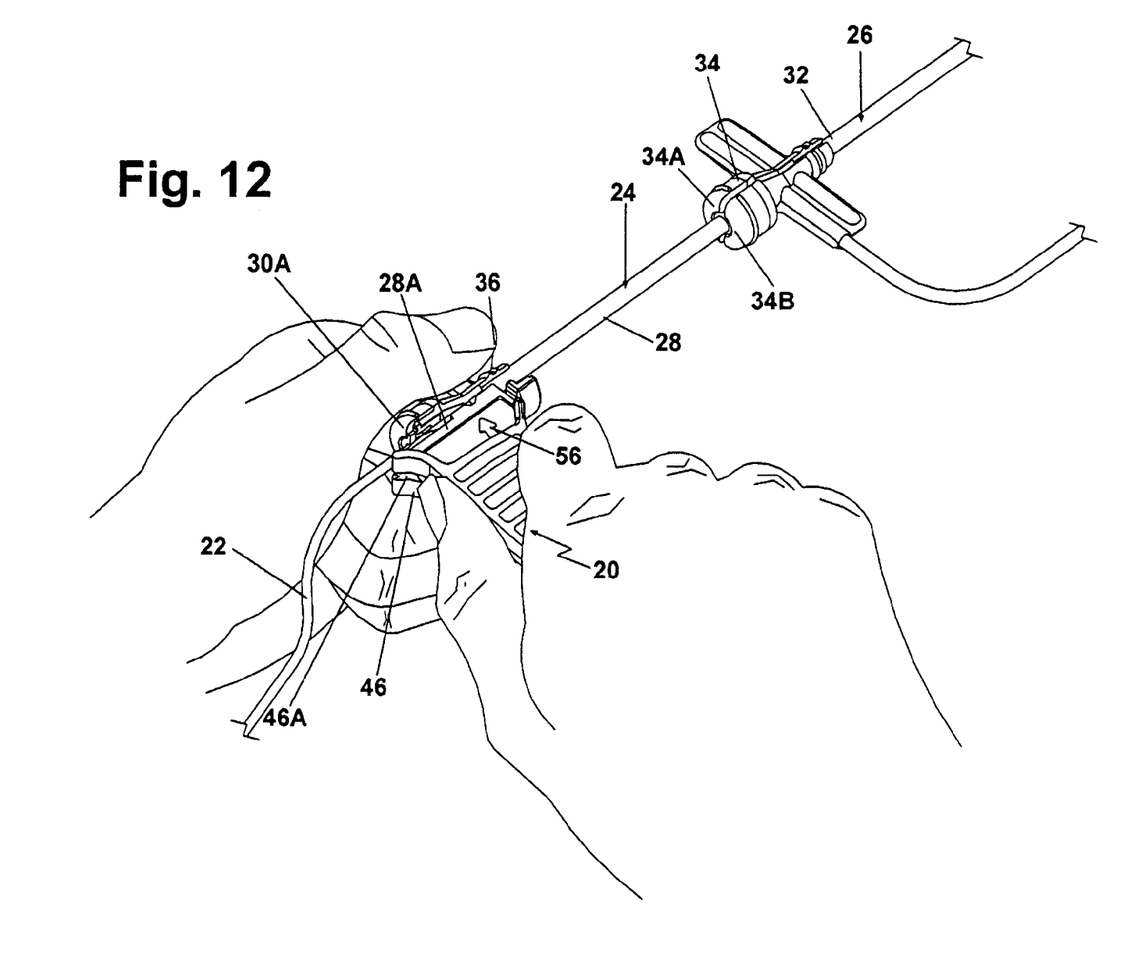
FIG. 12 is an illustration, like that of FIGS. 10 and 11, but showing a still later step in the removal of the inner catheter/sheath.
Figure 14:
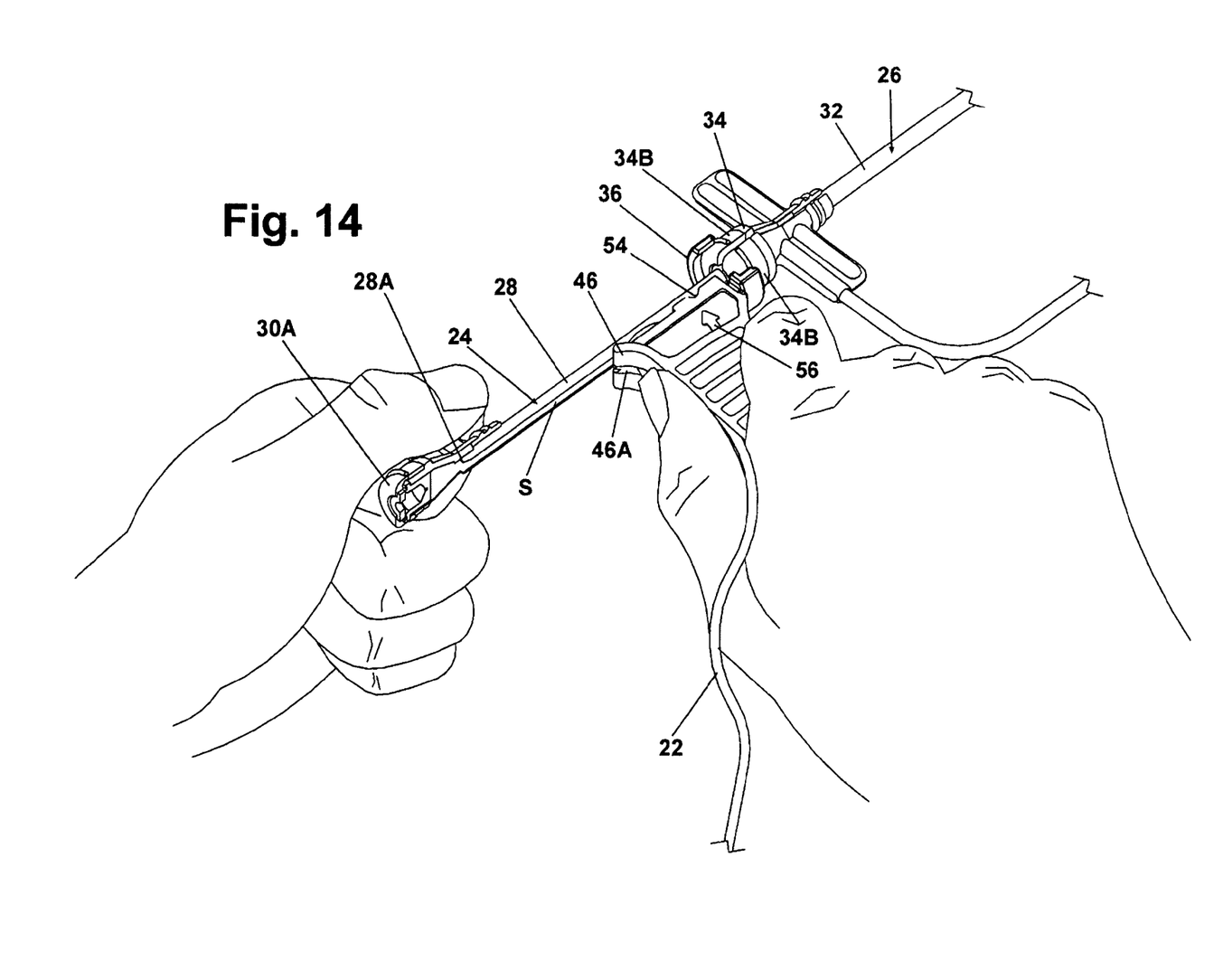
FIG. 14 is an illustration, like that of FIG. 10-13, but showing a still later step in the removal of the inner catheter/sheath.

As will be described in considerable detail later, particularly with reference to FIGS. 11 and 12, the splitting/slicing device 20 of this invention is used to receive the proximal end 28A of the tubular body 28 of the inner catheter/sheath 24, while holding the outer catheter/sheath 26 in place so that the user can pull the inner catheter/sheath 24 in the proximal direction with one hand while holding the pacing lead 22 in place with the thumb of his/her other hand as shown in FIG. 14. This action slits (cuts) the tubular body 28 of the inner catheter/sheath 24 longitudinally.

As mentioned earlier the hub 30 of the inner catheter/sheath 24 maybe constructed of two splitable sections 30A and 30B that can be readily separated or split from each other by the user applying a force to them to expose the proximal end 28A of the tubular body. The physician can then begin to cut or slice the tubular body 28 longitudinally by pulling on the inner catheter/sheath 24 in a proximal direction. During this cutting action the physician may stabilize or hold the pacing lead 22 at the desired position with one hand, while he/she pulls or otherwise withdraws the catheter/sheath out of the patient's body in one natural motion with the other hand.

As will also be described later the device 20 also includes a retainer portion 36 for engaging the hub 34 of the outer catheter/sheath 26 during the cutting of the tubular body of the inner catheter/sheath as shown in FIGS. 1 and 14. The action of the retainer 36 on the hub 34 of the outer catheter/sheath 26 automatically stabilizes or holds the outer catheter/sheath 26 in position. The cutting or slitting action of the device 20 is accomplished by a cutter 38 (FIGS. 1-4 and 6-9) which automatically cuts or slits the body 28 of the catheter/sheath longitudinally as it is withdrawn past the cutter 38, while the retainer portion 36 of device 20 holds the hub 34 of the outer catheter/sheath 26 in its desired position and while the thumb of the physician holds a proximal end portion of the pacing lead 22 within a proximal portion 40D of a groove 40 (FIG. 9A). Since the splitting device 20 of this invention accomplishes the dual action of stabilizing the pacing lead 22 and outer catheter/sheath 26 (if the procedure involves use an outer catheter/sheath—like shown in FIGS. 1 and 10-14) while facilitating the splitting and removal of the inner catheter/sheath 24 in one operation, the splitter device of this invention may be thought of to hereinafter as a "tear-away assist stabilizer" device.

Figure 7:
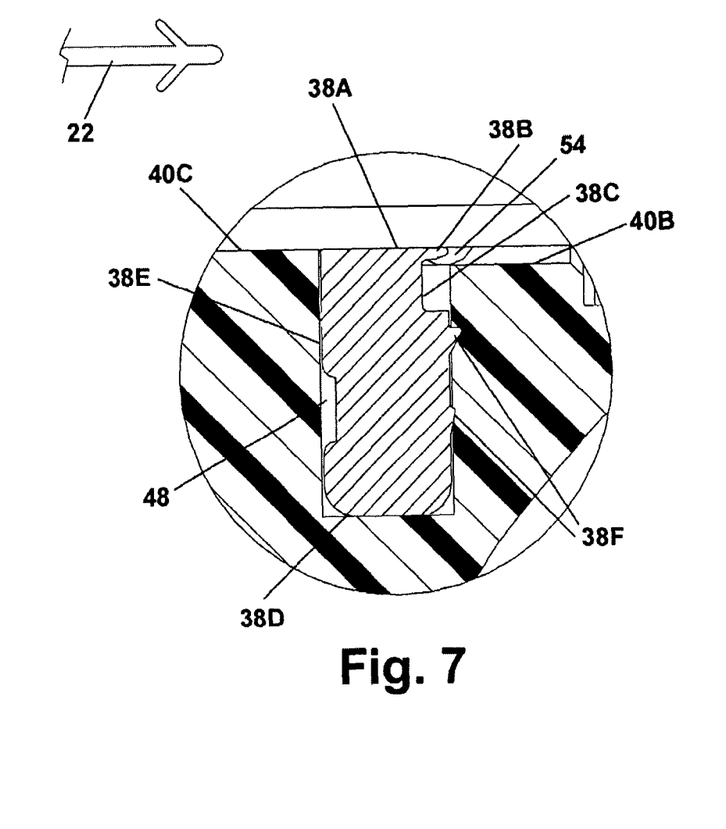
FIG. 7 is an is an enlarged vertical sectional view of the cutting portion of the device shown in FIG. 6.
Figure 8:
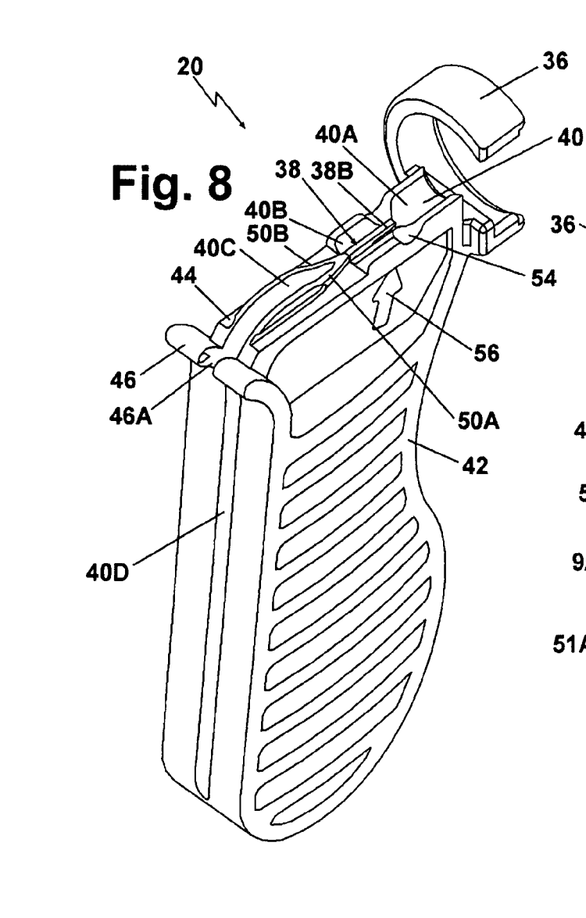
FIG. 8 is a top isometric view of the device of FIG. 1.
Figures 9, 9A:
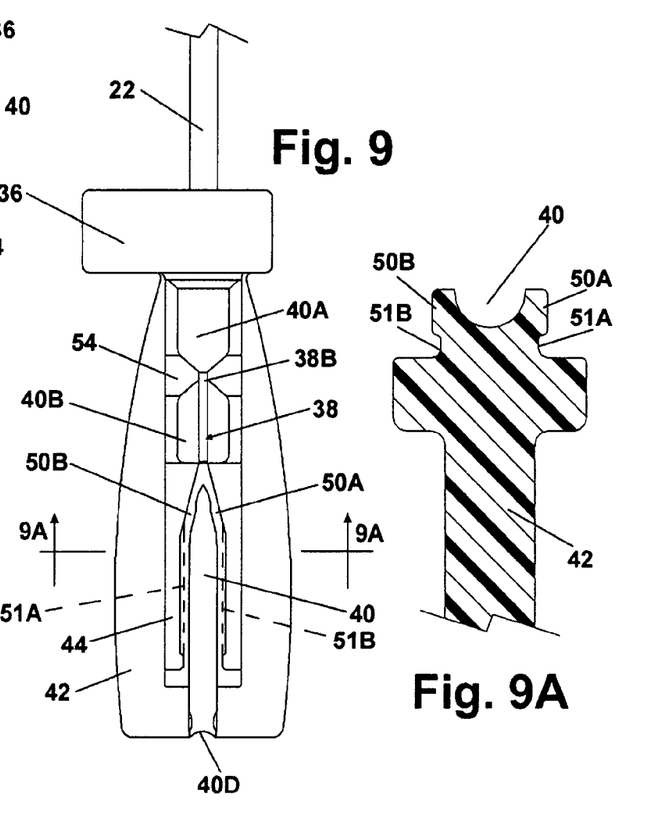
FIG. 9 is a top plan view of the device of FIG. 8.
FIG. 9A is an enlarged sectional view taken along line 9A-9A of FIG. 9.

Referring now to FIGS. 1 and 3-9, the details of the splitting device 20 will now be described. To that end the device 20 basically comprises a handle or hand grip portion 42, the heretofore identified cutter member 38, the heretofore identified retaining portion 36 and the heretofore identified groove 40. The handle 42 is somewhat pistol shaped to ergonomically fit comfortably in one hand of the user and includes a top surface 44 (FIGS. 8 and 9) in which three sections of the groove 40 (to be described hereinafter) are located. The retaining portion basically comprises a generally C-shaped ring located at the distal end of the top surface 44 of the device 20. The proximal end of the top surface 44 of the device is in the form of an concave arcuate wall 46 (FIGS. 1, 3 and 8) for receipt of the tip of the thumb of the user as will be described later. The wall 46 is split by a central notch 46A (FIG. 8).

As best seen in FIGS. 8 and 9 the groove 40 extends linearly centered along the top surface 44 of the device from the retaining ring 36 through the notch 46A in the arcuate wall 46 and downward along the proximal side of the handle 42. The groove is made up of a plurality of sequentially located sections, each of which is linear but somewhat different in cross-sectional shape. In particular, the proximal end section of the groove 40 is designated by the reference number 40A and is of constant semicircular cross-section along its length, with its radius of curvature being approximately that of the radius of curvature of the outer surface of the tubular body 28 of the inner catheter/sheath 24 in order to receive the tubular body 28 therein. The next successive or intermediate section of the groove 40 is designated by the reference number 40B and is also of constant semicircular cross-section along its length, with its radius of curvature being approximately that of the radius of curvature of the outer surface of the tubular body 28 of the inner catheter/sheath 24 in order to receive the tubular body 28 therein. The next successive or proximal top section of the groove 40 is designated by the reference number 40C and is of constant semicircular cross section along most of its length, except for its distal end. The radius of curvature of the constant cross-section portion of the groove sections 40C is approximately that of the radius of curvature of the outer surface of the pacing lead 22 in order to receive the pacing lead therein. The distal end portion of the groove section 40C flares outward from its distal end to its main constant semicircular cross-section portion to act as an entryway thereto. A pair of upstanding walls 50A and 50B are contiguous with the margins of the groove section 40C. Thus, the walls 50A and 50B flare outward from their proximal end to the point at which the groove section 40C assumes its constant semicircular cross-sectional shape and continue generally parallel to each other to a point closely adjacent the arcuate split wall 46. The groove section 40C, itself, extends from its flared distal end to the proximal end of the top surface 44, through the notch 46A in the arcuate wall 46. From that point the groove 40 includes a section 40D of constant semicircular cross-section that extends downward along the or rear or proximal edge of the handle 42. The radius of curvature of the groove section 40D is also approximately that of the radius of curvature of the outer surface of the pacing lead 22. As best seen in FIGS. 9 and 9A, an under-cut slot 51A extends longitudinally in the outer surface of the wall 50A. A similar under-cut slot 51B extends longitudinally in the outer surface of the wall 50B. The function of these slots will be described later.

The cutting member 38 is located at the interface of groove sections 40B and 40C. Referring now to FIGS. 4, 6, 7 and 8 the details of the cutting member 38 will now be described. The cutting member basically comprise a thin, flat plate of any suitably hard and tough material, e.g., stainless steel. As best seen in FIGS. 7 and 8, the plate 38 is of generally rectangular shape and includes a linear top edge 38A from which a finger 38B projects in the distal direction, a front or distal edge including a notch 38C, a bottom edge 38D and a rear or proximal edge 38E. The notch 38C is located immediately below the finger 38B and its vertical edge forms a cutting or knife blade. The cutting plate 38 is located with a recess 48 in the handle 42. The top of the recess 48 communicates with the bottom of the groove sections 40B and 40C. The cutting member 38 is held in place in the recess of the handle by means of extending projections or tangs 48F. The top edge 38A of the cutting member is flush with the top surface of the walls 50A and 50B where they merge together. The distally located finger 38B projects over the bottom of the groove section 40B to form a slot or space exposing a portion of the cutting edge 38C. The height of this slot or space is just slightly greater than the thickness of the tubular body 28 of the inner catheter/sheath 24 to accommodate the tubular body therein.

As should be appreciated by those skilled in the art the foregoing construction of the cutting member and its location as just described enables it to readily cut or slice a slit S (FIGS. 13 and 14) longitudinally along any catheter/sheath or other tubular member brought into groove 40 at section 40A and pulled down that groove in the proximal direction. In particular, with respect to the cutting or slicing of the tubular body 28 of the inner catheter/sheath 24, the proximal end 28A is inserted into groove section 28A and pulled rearwardly (proximally) until it fits under the finger 38A of the cutting member. Continued pulling on the tubular body 28 in that direction brings its end 28A into engagement with the knife edge 38C, which starts cutting or slitting the tubular body. The location of the finger between the inner surface of the tubular body 28 and the outer surface of the pacing lead 22 protects the pacing lead from injury. Continued pulling of the tubular body in the proximal direction brings the now spit proximal end thereof to the outer surface of the outwardly flaring walls 50A and 50B and into the under-cut slots 51A and 51B, to open the slit S, thereby exposing the pacing lead 22, which then enters into the proximal end portion of the groove section 40C. The under-cut slots 51A and 51B serve to retain the free edges of the tubular body contiguous with the slit S. Continued pulling of the tubular body 28 continues the slitting of that body along its length. The pacing lead in the meantime extends through the notch 46A in the arcuate wall 46 and down the groove section 40D.

In order to expedite the use of the device 20, it includes a semicircular notch 54 (FIG. 7) located in the top surface 44 at the location of the finger 38B of the cutting member to enable the user to readily visualize that portion of the cutting member. This enables the user to accurately insert the proximal end 28A of the catheter/sheath to be split under the finger 38B and into engagement with the cutting edge 38C. Indicia in the form of an arrow 56 is provided on the handle to point to the notch 54 and the cutting member 38.

Figure 3:
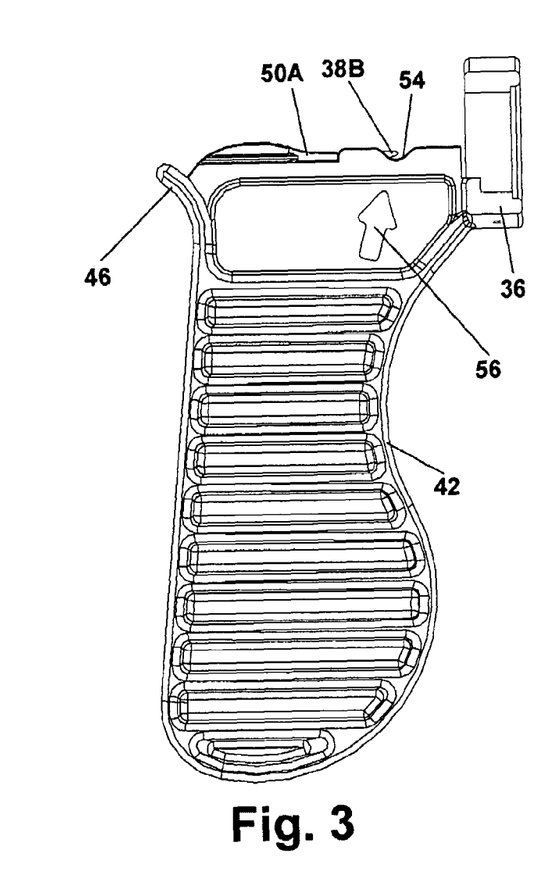
FIG. 3 is a side elevation view of the device of FIG. 1.
Figure 4:
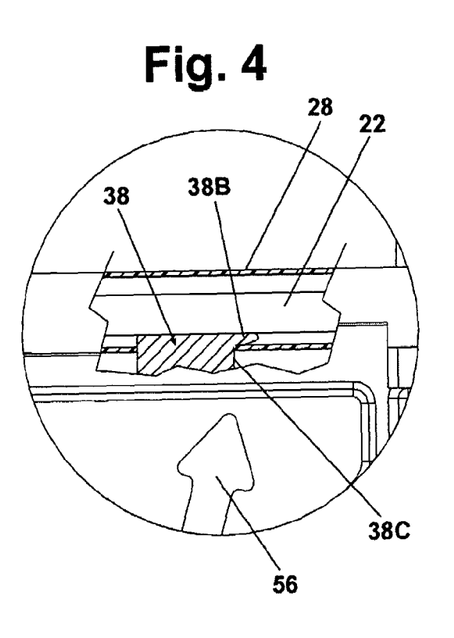
FIG. 4 is an enlarged side view, partially in section, of the cutting portion of the device of FIGS. 1.
Figure 5:
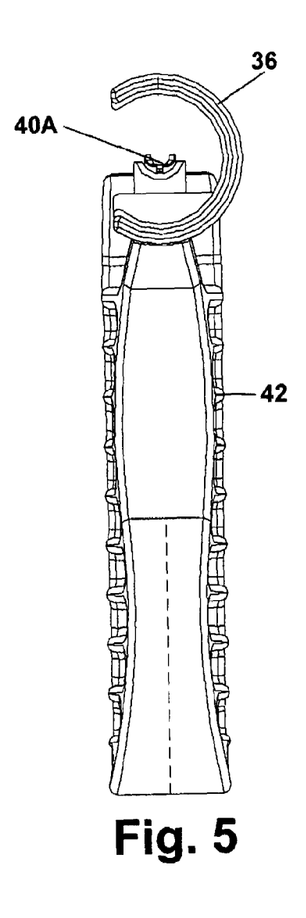
FIG. 5 is a front elevation view of the device of FIG. 1.
Figure 6:
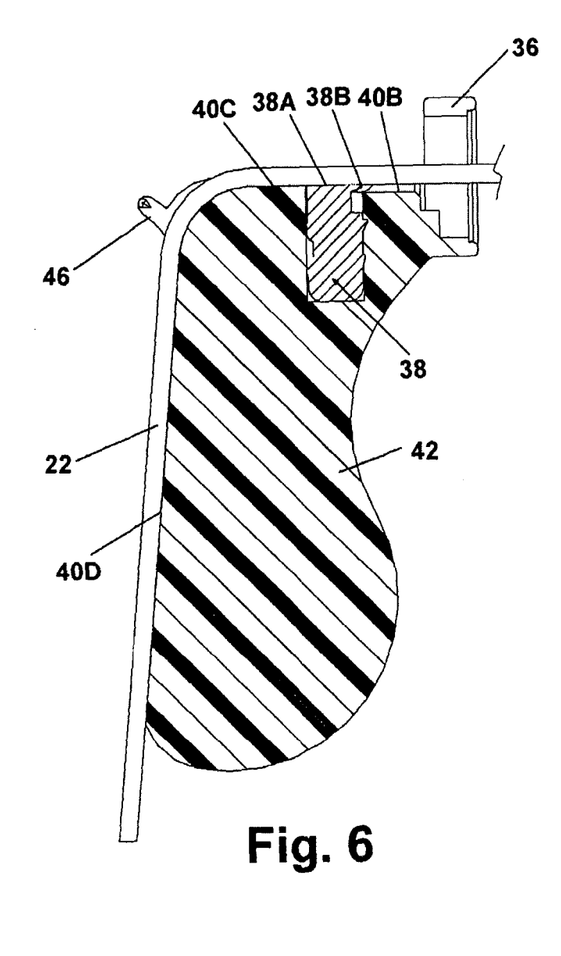
FIG. 6 is vertical sectional view of the device shown in FIG. 3.

Referring now to FIGS. 3 and 5 the details of the retainer ring 36 will now be described. As can be seen the ring 36 is of a generally C-shape to form a side gap or entry slot into which the catheter/sheath to be split maybe introduced laterally. The inner surface of the C-shaped ring is profiled to accept the hub of the outer catheter/sheath 26. Not only does the retainer ring 36 serve as a means for stabilizing the outer catheter/sheath (as will be described later), it also serves as a guide to straighten the curved distal end of the outer catheter/sheath as it is withdrawn from the patient's body, as will also be described later.

The following constitutes one exemplary method of using the device 20 of this invention. Once the pacing lead 22 has been located in its desired position, like described above, the hub 30 of the inner catheter/sheath 24 will be located some distance proximally of the hub of the outer catheter/sheath 26. The physician (or other user) then splits the hub 30 of the inner catheter/sheath 24 by grasping it and applying a manual force to it, such as shown in FIG. 10, to cause it to split apart into two separate sections 30A and 30B. Section 30A remains secured to the tubular body 28 and exposes its proximal end 28A. If the hub of the inner catheter/sheath 24 is constructed to include a thin (reduced) longitudinally extending walled portion, the device 20 of this invention may be used to cut that portion of the hub. Such action is accomplished by the physician holding the hub of the inner catheter/sheath in one hand and the splitter device 20 in the other hand and pushing on the splitter device (or pulling on the hub) so that its cutting blade edge 38C engages and slits the thin walled portion of the hub. The hub is then separated longitudinally along the cut line to expose the proximal end 28A of the tubular body 28 of the catheter/sheath. If the hub is a single sided one, the proximal end 28A of the tubular body will already be exposed.

Once the proximal end 28A of the tubular body of the inner catheter/sheath 24 is exposed, physician can then utilize the device 20 to begin to cut or slit that tubular body longitudinally. As shown in FIG. 11 this is accomplished by inserting the catheter/pacing lead assembly (i.e., the two catheter/sheaths with the pacing lead extending therethrough) laterally through the opening of the retaining ring 36 and locating the exposed proximal end 28A of the tubular body confronting the cutting member 38. The physician then manipulates the hub section 30A and the device 20 using the arrow indicia 56 so that the finger 38B of the cutting member 38 is located in the annular space between the inner surface of the tubular body of the inner catheter/sheath 28 and the outer surface of the pacing lead 22. The groove 54 in the handle provides the physician with a clear line of sight to the finger 38A. When this action has been accomplished the cutting edge 36C is disposed confronting the proximal end 28A of the tubular body of the inner catheter/sheath.

Figure 13:
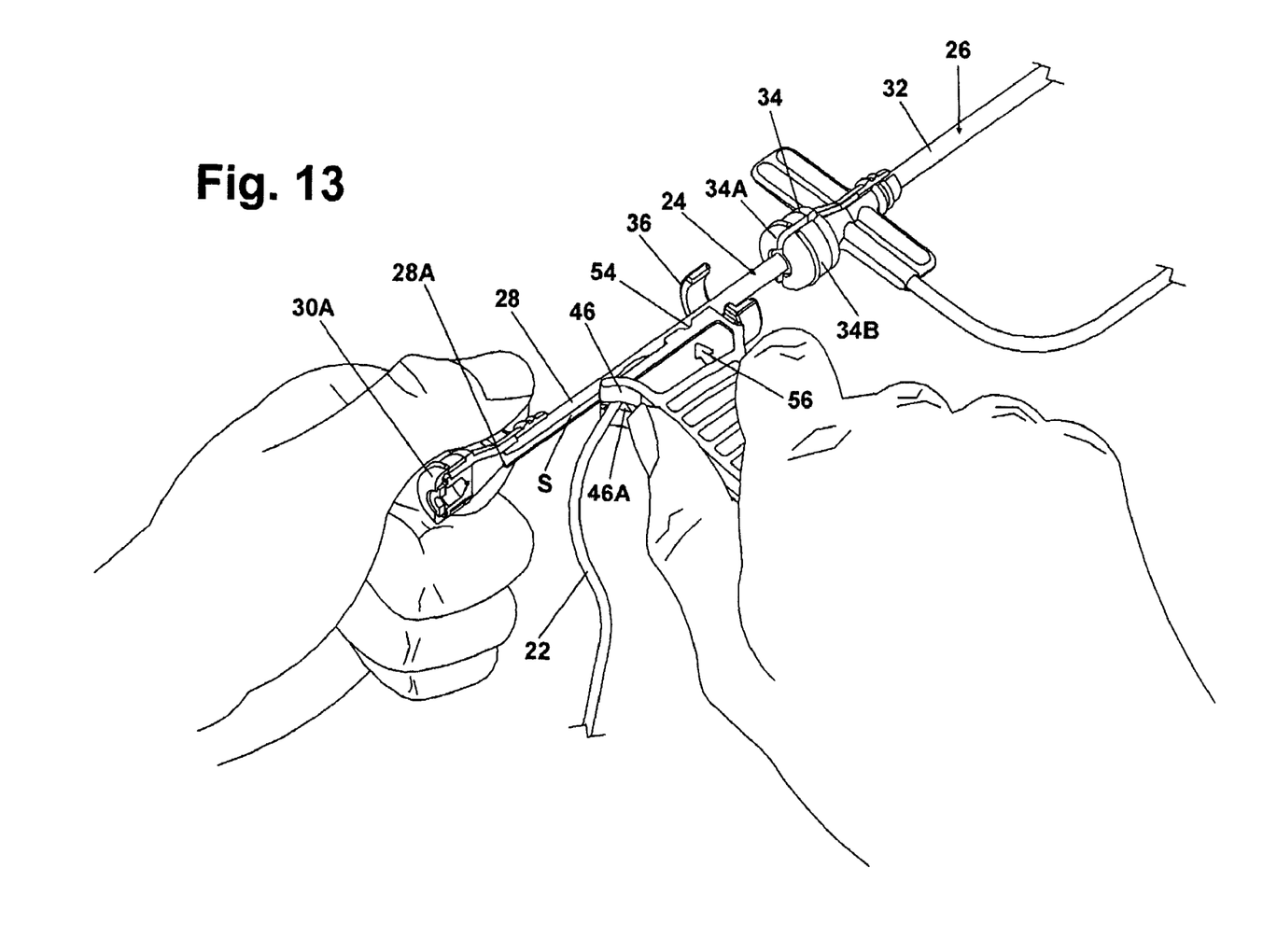
FIG. 13 is an illustration, like that of FIGS. 10-12, but showing a still later step in the removal of the inner catheter/sheath.

As best seen in FIG. 13 cutting or severing of the tubular body 28 is accomplished by the physician pulling on the hub section 30A of the inner catheter/sheath 24 in a proximal direction with one hand while holding the device 20 in the other hand, whereupon the cutting blade 38C cuts into the tubular body 28 of the inner catheter/sheath. At this time the physician does not apply any pressure through his/her thumb on the pacing lead 22 extending out of the notch 46A in the arcuate wall 46. The continued pulling on the inner catheter/sheath splits or cuts its body 28 longitudinally while the flaring walls 50A and 50B cause the longitudinal cut to open or separate to form a longitudinally extending slot S. The continued pulling on the inner catheter/sheath also causes the outer catheter/sheath 26 to move in the proximal direction relative to the device 20 until the hub 34 of the outer catheter/sheath 26 engages and is received within the retainer ring 36 as shown in FIG. 14. Once this has occurred the outer catheter/sheath 26 will be automatically stabilized in position by the retainer ring 36. The physician can then apply manual pressure through his/her thumb onto the pacing lead 22 portion within the proximally located groove portion 40D to stabilize or hold the pacing lead at the desired position with one hand, while he/she pulls or otherwise withdraws the inner catheter/sheath 24 out of the patient's body in one natural motion with the other hand.

Once the inner catheter/sheath 24 has been removed from the patient's body as just described, the outer catheter/sheath is ready for removal. Depending upon the construction of the outer catheter/sheath 26, such action can be accomplished in various manners. For example, if the outer catheter/sheath 26 is constructed to be inherently splitable, e.g., the body includes at least one longitudinally weakened or frangible line which can be broken by the application of a force to it, the outer catheter/sheath can be removed by splitting it and pulling it out of the patient's body while holding the pacing lead in place. If, however, the body of the outer catheter/sheath 26 is not inherently splitable, such as is the case with a braided reinforced sheath like that described above with respect to catheter/sheath 24, then the device 20 of this invention is used to slit the tubular body 32 of the catheter/sheath 26 in a similar manner as described above. As should be appreciated by those skilled in the art, when the extraction of the outer catheter/sheath 26 is being accomplished, the retainer ring 36 serves as a guide to straighten the curved distal end of the outer catheter/sheath as it is withdrawn from the patient's body through the ring. This facilitates the removal of the outer catheter/sheath from the patient's body.

Figure 2:
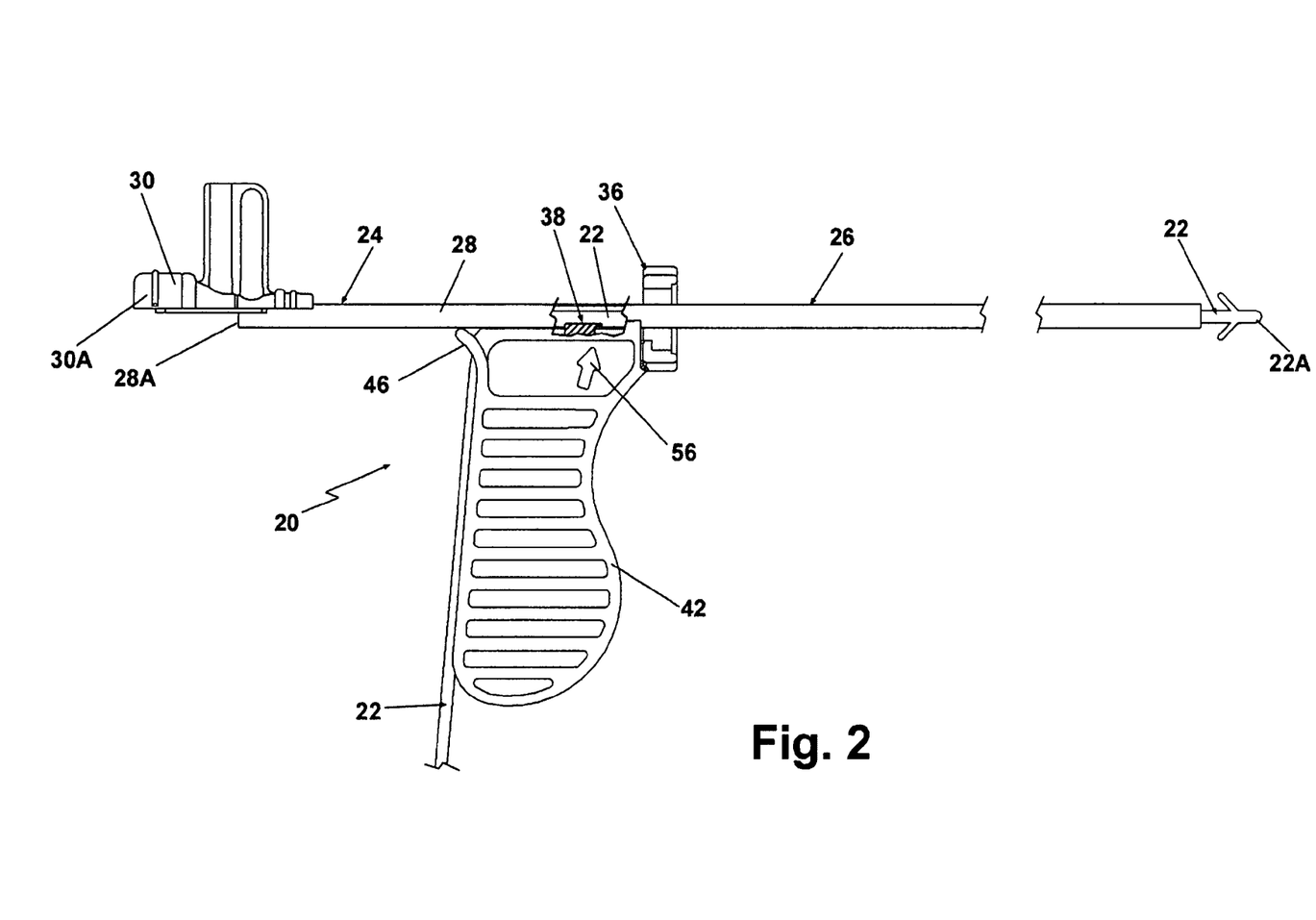
FIG. 2 is a view similar to FIG. 1, but showing the device of FIG. 1 but used with a conventional cardiac pacing lead located extending through only a single catheter/sheath.

It should be pointed out at this juncture that the device 20 need not be used with a dual catheter/sheath system like that described above. In particular, it can be used for splitting a single, reinforced catheter/sheath through which a pacing lead extends. Such an arrangement is shown in FIG. 2. In such a case the operation of the device is the same as described above, except that the retaining ring is not needed, since there will be no outer catheter/sheath needing stabilization. In the interest of brevity the operation of the device 20 to effect the splitting and removal of the single catheter/sheath 24 will not be reiterated.

It should also be pointed out that while the subject invention is particularly useful for splitting reinforced (e.g., braided) catheter/sheaths, it can be used for cutting any tubular member longitudinally while stabilizing an elongated device or instrument extending through the tubular member.

While the invention has been described in detail and with reference to specific examples thereof, it will be apparent to one skilled in the art that various changes and modifications can be made therein without departing from the spirit and scope thereof.

We claim:

1. A device for slitting a first elongated flexible catheter used with an elongated flexible component, the first catheter having an interior surface, the elongated flexible component having an exterior surface and being arranged to be extended through the first catheter, whereupon an annular space between the inner surface of the first catheter and the outer surface of the elongated flexible component results, said device comprising a handle, a receiving surface and a cutter member, said receiving surface having a longitudinal axis and being arranged to receive a proximal end portion of the outer periphery of the first catheter thereon, said cutter member having a bottom portion, a top portion spaced from said bottom portion and a sharp distally located cutting edge between said bottom portion and said top portion, said cutter member projecting upward from a first recessed portion of said receiving surface with said bottom portion of said cutter member being immediately adjacent said first recessed portion, said top portion of said cutter member having a finger projecting in a distal direction beyond said distally located cutting edge to form a gap between said finger and said first recessed portion of said receiving surface, said first recessed portion of said receiving surface being shaped to accommodate and hold a portion of the periphery of the first catheter in said gap, said finger overhanging said distally located cutting edge and being arranged to be located within the annular space between the elongated flexible component and the first catheter when the first catheter is disposed within said gap, said distally located cutting edge being arranged to slit the first catheter when the device is moved with respect to the first catheter in a distal direction and with said finger protecting the elongated flexible component from said cutting edge.

2. The slitting device of claim 1 wherein said receiving surface comprises a groove, said groove including a distally located portion and a proximally located portion, said distally located portion of said groove being shaped to accommodate a portion of the periphery of the outer surface of the first catheter therein, said proximally located portion of said groove being shaped to receive a portion of the periphery of the outer surface of the component therein as the first catheter is slit to enable the thumb of a user of said slitting device to hold the component in place.

3. The slitting device of claim 2 wherein said groove includes a portion having a pair of contiguous walls flaring in a proximal direction, said walls being arranged to separate the slit portions of the first catheter.

4. The slitting device of claim 3 wherein each of said contiguous walls includes an undercut recess therein for retaining a respective one of the slit portions of the first catheter.

5. The slitting device of claim 2 wherein said distally located portion of said groove is of an arcuate cross section and wherein said proximally located portion of said groove is of an arcuate cross section.

6. The slitting device of claim 5 wherein said distally located portion of said groove is of a semicircular cross-section having a radius of curvature approximately equal to that of the outer surface of the first catheter, and wherein said proximally located portion of said groove is of a semicircular cross-section having a radius of curvature approximately equal to that of the outer surface of the component.

7. The slitting device of claim 6 wherein said groove includes a portion having a pair of contiguous walls flaring in a proximal direction, said walls being arranged to separate the slit portions of the first catheter.

8. The slitting device of claim 3 wherein each of said contiguous walls includes an undercut recess therein for retaining a respective one of the slit portions of the first catheter.

9. The slitting device of claim 1 wherein the first catheter has a generally curved distal end portion and wherein said device additionally comprises a member located adjacent the distal end portion of said receiving surface for engaging the generally distal end portion of the first catheter to straighten it as the first catheter is moved with respect to said receiving surface in a proximal direction along said receiving surface.

10. The slitting device of claim 9 wherein said member comprises a C-shaped wall forming a portion of a circle and having a gap, with the center of said circle being coaxial with said longitudinal axis of said receiving surface and with said gap being located laterally of said longitudinal axis.

11. TIhe slitting device of claim 1 wherein said slitting device is arranged to be used with a second catheter, the second catheter being arranged to be extended into the body of the being, with the first catheter extending through the second catheter, the second catheter comprising a hub and wherein said slitting device additionally comprises a retaining member located adjacent a distal end portion of said receiving surface, said retaining member being adapted to receive and hold the hub of the second catheter.

12. The slitting device of claim 2 wherein said slitting device is arranged to be used with a second catheter, the second catheter being arranged to be extended into the body of the being, with the first catheter extending through the second catheter, the second catheter comprising a hub and wherein said slitting device additionally comprises a retaining member located adjacent the distal end portion of said groove and adapted to receive and hold the hub of the second catheter.

13. The slitting device of claim 9 wherein said slitting device is arranged to be used with a second catheter, the second catheter being arranged to be extended into the body of the being, with the first catheter extending through the second catheter, the second catheter comprising a hub and wherein said member is a retaining member adapted to receive and hold the hub of the second catheter.

14. The slitting device of claim 11 wherein said retaining member comprising a generally C-shaped wall forming a portion of a circle, with the center of the circle being coaxial with said longitudinal axis of said receiving surface.

15. The slitting device of claim 12 wherein said retaining member comprising a generally C-shaped wall forming a portion of a circle, with the center of the circle being coaxial with said groove.

16. The slitting device of claim 13 wherein said retaining member comprising a generally C-shaped wall forming a portion of a circle, with the center of the circle being coaxial with said longitudinal axis of said receiving surface.

17. The sliffing device of claim 1 wherein said distally located cutting edge is formed of metal or ceramic.

18. The slitting device of claim 2 wherein said distally located cuffing edge is formed of metal or ceramic.

19. The slitting device of claim 8 wherein said distally located cutting edge is formed of metal or ceramic.

* * * * *